United States Patent [19]

Wong et al.

[11] Patent Number: 5,447,865
[45] Date of Patent: Sep. 5, 1995

[54] METHOD OF RESOLUTION OF HYDROXY SUBSTITUTED CYCLOPENTANONE ENANTIOMERS USING LIPASE AND LITHIUM SALT COMPLEXATION

[75] Inventors: Patrick Y-K Wong, York Town, N.Y.; Bernd W. Spur, Mönchengladbach, Germany

[73] Assignee: Amprost Pharmaceutical, Inc., Yorktown, N.Y.

[21] Appl. No.: 185,442

[22] Filed: Jan. 24, 1994

Related U.S. Application Data

[63] Continuation of Ser. No. 896,119, Jun. 10, 1992, abandoned.

[51] Int. Cl.$^6$ .............................................. C12P 41/00
[52] U.S. Cl. ...................................... 435/280; 435/136
[58] Field of Search ................................ 435/280, 136

[56] References Cited

U.S. PATENT DOCUMENTS

| | | | |
|---|---|---|---|
| 3,953,499 | 4/1976 | Pike et al. | 260/514 D |
| 4,237,316 | 12/1980 | Bernady et al. | 562/503 |
| 4,452,994 | 6/1984 | Hill et al. | 560/121 |
| 4,493,635 | 7/1990 | Corey | 546/13 |
| 4,987,236 | 1/1991 | Sato | 549/208 |

FOREIGN PATENT DOCUMENTS

| | | |
|---|---|---|
| 0255379A2 | 2/1988 | European Pat. Off. . |
| 0298756A2 | 1/1989 | European Pat. Off. . |
| 0357009A2 | 3/1990 | European Pat. Off. . |
| 2323137 | of 0000 | Germany . |

OTHER PUBLICATIONS

Fitzpatrick, P et al, J Am Chem Soc 113:3166-371 (1991).
Wang, Y-F, et al, J Am Chem Soc 110:7200-05 (1988).
Klibanov A, Chem Tech 354-59 (1986).
Zaks A et al, Proc. Natl. Acad. Sci 82:3192-96 (1985).
Okumura S et al, BBA 575:156-165 (1979).
Hills M J et al, BBA 1042:237-40 (1990).
Charles J. Sih et al. (1972) *J. Am. Chem. Soc.*, vol. 94(10), pp. 3643-3644.
Arthur F. Kluge et al. (1972) *J. Am. Chem. Soc.*, vol. 94(22), pp. 7827-7831.
John J. Partridge et al. (1973) *J. Am. Chem. Soc.*, vol. 95(21), pp. 7171-7172.
Charles J. Sih et al. (1975) *J. Am. Chem. Soc.*, vol. 97(4), pp. 865-874.
K. C. Nicolaou et al. (1984) *J. Am. Chem. Soc.*, vol. 106(12), pp. 3548-3551.
K. C. Nicolaou et al. (1985) *J. Am. Chem. Soc.*, vol. 107(25), pp. 7515-7518.
Frank H. Lincoln et al. (1973) *J. Org. Chem.*, vol. 38(5), pp. 951-956.
Masateru Miyano et al. (1975) *J. Org. Chem.*, vol. 40(12), pp. 1748-1755.
Sentaro Okamoto et al. (1988) *J. Org. Chem.*, vol. 53(23), pp. 5590-5592.
Kevin A. Babiak et al. (1990) *J. Org. Chem.*, vol. 55(10), pp. 3377-3381.
Yuichi Kobayashi et al. (1990) *J. Org. Chem.*, vol. 55(19), pp. 5324-5335.
John H. Dygos et al. (1991) *J. Org. Chem.*, vol. 56(7), pp. 2549-2552.
R. Noyori et al. (1990) *Chemtracts-Organic Chemistry*, pp. 173-197.
Wilhelm Boland et al. (1991) *Synthesis*, pp. 1049-1072.
Patrick Y-K Wong et al. (1979) *European J. of Pharmacology*, vol. 60, pp. 245-248.
Melvyn Gill et al. (1981) *Aust. J. Chem.*, vol. 34, pp. 1063-1071.
Wei Kuo Lin et al. (1990) *Biochem. & Biophy. Res. Comm.*, vol. 167(3), pp. 977-981.

*Primary Examiner*—Marian C. Knode
*Assistant Examiner*—S. Saucier
*Attorney, Agent, or Firm*—Darby & Darby

[57] ABSTRACT

A method for the resolution of optically active compounds from racemic mixtures is provided. In one embodiment of the method, racemic substituted cyclopentenones, useful as eicosanoid intermediates, are enzymatically resolved with lipase and separated by formation of lithium salt complexes. In another embodiment of the method, optically active alcohols are obtained from prochiral halovinyl ketones or alkynyl ketones by selective catalytic reduction with chiral boronic catalysts. In yet another embodiment of the method, prostaglandin $E_1$ are produced from prostaglandin $E_1$ esters by selective ester hydrolysis with a lipase.

17 Claims, 5 Drawing Sheets

METHOD OF RESOLUTION OF HYDROXY SUBSTITUTED CYCLOPENTANONE ENANTIOMERS USING LIPASE AND LITHIUM SALT COMPLEXATION

This is a continuation, of application 07/896,119 filed Jun. 10, 1992 now abandoned.

FIELD OF THE INVENTION

This invention relates to a method for the preparation and recovery of optically active organic compounds from complex reaction mixtures which avoids the extensive use of chromatography. In particular, this invention relates to a method of resolving and isolating optically active pharmaceuticals and intermediates thereof.

BACKGROUND OF THE INVENTION

Eicosanoids are naturally occurring, optically active, bioactive metabolites which are produced by metabolism of arachidonic acid, the predominant 20-carbon fatty acid found in mammalian tissues. The investigation of prostaglandins (PG), thromboxanes (TX), lipoxins (LX) and leukotrienes (LT), collectively known as eicosanoids, has led to important advances in synthetic organic chemistry, biochemistry, and physiology.

Chemical methods for synthesizing and isolating optically active intermediates for use in preparing eicosanoids are known in the art. For example, Kobayashi et al. (1990) *J. Org. Chem.*, Vol. 55, pages 5324–5335; Okamoto et al. (1988) *J. Org. Chem.*, Vol. 53, pages 5590–5592; and Nicolau et al. (1985) *J. Amer. Chem. Soc.*, Vol. 107, pages 7515–7518 describe the application of the Sharpless kinetic resolution, using titanium complexes, of racemic intermediates for synthesis of leukotriene B$_4$, prostaglandins, and lipoxin A$_4$, respectively. Similarly, Nori et al. (1990) *Chemtracts*, pages 173–197 describes the application of chiral reductive organometallic complexes for synthesizing prostaglandin chiral ancillary intermediates. In general, these methods suffer from a variety of deficiencies which include complicated multistep syntheses involving costly chiral reagents as well as complicated chemical resolution of racemic mixtures. More significantly, compounds having mediocre enantiomeric purities are produced.

Biocatalylic methods have been also applied towards the preparation and resolution of racemic eicosanoid intermediates. These methods exploit the regio- and stereo-selectivity of enzymes. The types of enzymes which are useful as biocatalysts and methods for their use in the preparation of optically pure compounds have been described in the literature. For a review, see, W. Boland et al. (1991) *Synthesis*, pages 1049–1072.

K. A. Babiak et al. (1990) *J. Org. Chem.*, Vol. 55, pages 3377–3381 and EP application No. 0357009, for example, describe the resolution of racemic prostaglandin synthons, e.g. 4-hydroxy-2-alkyl-2-cyclopentenone, using lipase-catalyzed esterification reactions in the presence of vinyl acetate as organic solvent and acylating agent. Selective acylation of only one enantiomer occurs during the reaction, allowing isolation of optical isomers having enantiomeric excesses greater than 99%.

In practicing this resolution method, however, the crude reaction mixture, containing a mixture of diastereomers, must be immediately purified upon completion of the esterification reaction to prevent epimerization of the acylated derivative. Conventional purification methods such as column chromatography over silica gel is generally used for separating the diastereomers. While such purification methods are generally useful in small scale reactions, they are impractical for industrial scale operations.

Processes for isolating organic compounds from crude mixtures are known in the art. Among these methods, processes which involve preferential complexation of organic compounds with metal salts have been described. For example, U.S. Pat. No. 4,452,994 discloses the use of lithium salts for purifying prostaglandin racemates from crude reaction mixtures; U.S. Pat. No. 4,057,541 relates to the use of calcium salts for separating 3-hydroxy and 3-keto steroids from reaction mixtures; and Sharpless et al. (1975) *J. Org. Chem.*, Vol. 40, pages 1252–1257 relates to the use of calcium and manganese salts for preferential complexation with alcohols. These metal complexes have been used in processes for purification of racemates from complex reaction mixtures. However, prior to the present disclosure, there are no teachings or suggestions concerning the use of metal salt complexation as a means of separating enzymatically or chemically resolved optical isomers from crude reaction mixtures.

Accordingly, there is a need in the art for a practical method for recovering optical isomers from enzymatically resolved reaction mixtures which avoids at least one of the aforementioned deficiencies.

SUMMARY OF THE INVENTION

A method for enzymatic or chemical resolution and recovery of optically pure intermediates, which avoids the need for extensive chromatography, is provided.

It has been discovered that valuable optically pure eicosanoid intermediates can be obtained, in high yields and enantiomeric purities, by resolving a substituted cyclopentenone compound selected from the group consisting of:

wherein X represents alkyl, alkenyl or alkynyl groups having 2 to 10 carbon atoms and R is selected from the group consisting of —CH$_2$OR$_1$ and —CO$_2$R$_2$ wherein R$_1$ is selected from the group consisting of hydrogen; alkyl of 1 to 6 carbon atoms; ethoxyethyl; adamantyl; aryl; heteroaryl such as pyridine, quinoline, benzofuran, benzothiophene and thiophene; and heterocyclic such as tetrahydropyran, tetrahydrofuran and dioxane; and R$_2$ is alkyl of 1 to 6 carbon atoms, by a method comprising contacting the compound with an effective amount of a lipase and an effective amount of an acylating reagent, in the absence of water, so as to form the corresponding S alcohol and R acetate in mixture form. The mixture is then treated with a lithium salt, in the presence of a solvent, which forms a stable crystalline lithium salt complex with the S alcohol which is subsequently filtered out. The filtrate contains the diastereomeric derivative R acetate produced from the enzymatic reaction in >99% enantiomeric excess (ee). Optically pure S alcohol is recovered by subjecting the lithium salt complex to hydrolytic cleavage. The S alcohol may be converted to the R alcohol by a Mitsunobu inversion reaction.

It has also been discovered that PGE$_1$ can be obtained from a PGE$_1$ ester having the formula:

wherein R is selected from the group consisting of hydrogen; alkyl of 1 to 6 carbon atoms; adamantyl; β-oxo-carbonyl; aryl; heteroaryl such as pyridine, quinoline, benzofuran, benzothiophene, and thiophene; and heterocyclic such as tetrahydropyran, tetrahydrofuran, and dioxane, by a method comprising contacting said PGE$_1$ ester with an amount of a lipase, in the presence of organic solvent, which is effective for hydrolyzing the ester. Unlike conventional methods of hydrolysis, the lipase-catalyzed hydrolysis of the ester is highly selective and produces highly pure PGE$_1$.

It has been further discovered that chiral alcohols of halovinyl ketones (A) and alkynyl ketones (B), useful in the synthesis of eicosanoids, are obtained by reducing a compound of the formula:

wherein R$_9$ and R$_{10}$ are independently selected from the group consisting of hydrogen; alkyl, alkenyl or alkynyl having 2 to 10 carbon atoms; adamantyl; R$_3$R$_4$R$_5$Y wherein Y=Si or Sn and wherein R$_3$, R$_4$, and R$_5$ are independently selected from the group consisting of methyl, ethyl, isopropyl, t-butyl and phenyl; and X is selected from the group consisting of hydrogen, iodine, chloride, bromide, fluoride, and R$_6$R$_7$R$_8$Y wherein Y=Si or Sn and wherein R$_6$, R$_7$, and R$_8$ are independently selected from the group consisting of methyl, ethyl, isopropyl, t-butyl and phenyl, in a method comprising treating the compound with a chiral boronic catalyst in an molar ratio ranging between about 1:1 and about 1:0.01. Suitable examples of chiral boronic catalysts include N-alkyl or N-aryl boronic complexes of diphenyl D(−) or L(+) prolinols. These chiral catalysts produce enantiomers with very high ee values.

DETAILED DESCRIPTION OF THE INVENTION

All patents and literature references cited in this specification are hereby incorporated by reference in their entirety. In the case of inconsistencies, the definitions and disclosure of the present specification will prevail.

All chemical reagents and solvents referred to herein are commercially available from a variety of sources which include Aldrich Chemicals (Milwaukee, Wis., USA), Fluka (Switzerland) and Merck Co. (Germany).

The present invention arose from the discovery that optically active substituted cyclopentenone compounds, which are useful as intermediates in the synthesis of eicosanoids (e.g., prostaglandins (PGs) and their analogues and derivatives), selected from the group consisting of:

wherein X is selected from the group consisting of alkyl, alkenyl or alkynyl groups having 2 to 10 carbon atoms and R is selected from the group consisting of —CH$_2$OR$_1$ and —CO$_2$R$_2$ wherein R$_1$ is hydrogen; alkyl of 1 to 6 carbon atoms; ethoxyethyl; adamantyl; aryl; heteroaryl such as pyridine, quinoline, benzofuran, benzothiophene and thiophene; or heterocyclic such as tetrahydropyran, tetrahydrofuran, and dioxane; and R$_2$ is alkyl of 1 to 6 carbon atoms, are readily and advantageously isolated and purified from lipase-resolved mixtures by formation of lithium salt complexes in the presence of a suitable solvent.

The types of lipase enzymes and conditions for their use in methods for resolving racemic mixtures into optically active compounds have been described. For example, W. Boland et al. (1991); M. A. Findeis et al. (1984) *Ann. Reports in Med. Chem.*, Vol.19, pages 263–272 and P. F. Leadley in "An Introduction to Enzyme Chemistry", Monograph No. 32; London: The Chemical Society publishers, 1978, pages 67–82; K. A. Babiak et al. (1990); and EP application No. 0357009, describes enzymes which are useful as biocatalysts in organic reactions.

In practicing the invention, a racemic mixture of an organic compound, e.g. racemic substituted cyclopentenone, is contacted with an effective amount of a lipase and an effective amount of acylating reagent, in the absence of water and optionally in the presence of solvent, whereby the lipase selectively catalyzes the esterification of the R alcohol, producing a mixture of the R acetate and unreacted S alcohol.

Suitable, but non-limiting, examples of lipases include lipases derived from porcine pancreas, wheat germ, *Candida cylindracea*, *Rhizopus arrhizus*, *Chromobacterium viscosum*, *Geotrichum candidum*, *Rhizopus delamar*, and *Pseudomonas* species. These enzymes are commercially available from a number of sources which include Sigma Chemicals Co. (St. Louis, Mo.). A preferred lipase for use in the present invention is porcine pancreatic lipase.

In general, the amount (g) of lipase used per mole of racemate, e.g. substituted cyclopentenone compound, ranges between about 0.1% and about 200%, preferably between about 10% and about 90%.

Suitable, but non-limiting, examples of acylating agents for use in the reaction includes vinyl acetate, vinyl butyrate and vinyl valerate. A preferred acylating agent is vinyl acetate.

The molar ratio amount of acylating agent used per mole of racemic compound, e.g. substituted cyclopentenone compound, ranges between about 1 mole and about 1000 moles, preferably between about 10 and about 100 moles.

The enzymatic reaction is conducted at a temperature ranging between about 0° C. and about 60° C., preferably about 25° C., for a time period ranging between about 1 hour and about 14 days, preferably about 7 hours. The mixture is stirred throughout this period by conventional means which include mechanical stirring and shaking.

Optionally, the esterification reaction can be conducted in the presence of a solvent, although it is preferred to employ the acylating agent as a solvent. Suitable, but non-limiting, examples of solvents include alkanes such as pentane, hexane, heptane, and cyclohexanes; chlorinated alkanes such as methylene chloride; toluene and tetrahydrofuran (THF). The amount of solvent employed per mole of racemic compound, e.g. substituted cyclopentenone compound, ranges between about 1 mol and about 1000 mol, preferably about 20 mol.

Thereafter, the reaction mixture containing the enzymatically resolved diastereomers is separated from the suspended enzyme by conventional techniques which include filtration, centrifugation, and decantation.

The reaction mixture then is dissolved in any suitable non-hydroxylic organic solvent, e.g. ether, hexane, pentane, heptane or toluene, to form a solution and between about 1 mole and about 35 moles of lithium salt, preferably between about 1 mole and about 10 moles, per mole of product is added thereto. The lithium salt forms a stable crystalline lithium salt complex with the S alcohol and precipitates out of the solution.

Examples of suitable, but non-limiting, lithium salts that are useful in the invention include lithium bromide, lithium chloride, lithium iodide, lithium perchlorate, and lithium fluoroborate. A preferred lithium salt is lithium bromide.

The selection of solvent is primarily dependent upon the nature of the compound to be isolated and must be non-hydroxylic. Suitable, but non-limiting, examples of solvents include chlorinated solvents such as methylene chloride; hydrocarbons such as hexane, pentane, cyclohexanes and toluene; ethers such as tetrahydrofuran (THF); and ethyl acetate. The preferred solvents for use in practicing the invention are toluene, hexane and methylene chloride.

In practicing the invention, the complexation reaction is conducted for period of time and at selected temperatures which are effective to complete the reaction. Commonly, temperatures ranging between about $-10°$ C. and about 60° C., preferably ranging between about 0° C. and about 25° C., for between about 10 minutes and about 24 hours, preferably between about 30 minutes and about 6 hours, are utilized.

It has been found that certain lithium salts exhibit selectivity toward various functional groups and the choice of the particular lithium salt depends upon the nature of the substrate. For example, lithium bromide advantageously complexes alcohols, phenols, amides, imides, carboxylic acids primary and secondary amines, and sulfonides. These organic compounds contain free functional groups which are capable of complexing with the lithium salt. Non-limiting examples of free functional groups include hydroxyl, primary amino, secondary amino, amido, imido, and carboxylic acid. Lithium perchlorate advantageously complexes all of the above plus ketones and aldehydes. Thus the choice of the particular lithium salt is dependent on the particular substrate.

Under the aforementioned conditions, the lithium salt binds selectively to one of the two diastereomeric isomers which has a free functional group, e.g. the S alcohol, forming a complex which then precipitates out of the solution. This complex is removed by conventional methods, e.g. filtration, and placed in a large excess (between about 1 to about 100 moles) of water for an effective amount of time and at an effective temperature in order to cleave the complex and thus release the diastereomeric isomer.

The time and temperature for the cleavage step depend upon the nature of the compounds being isolated. The time and temperature generally utilized for cleaving the lithium salt are between about 10 minutes and about 6 hours at temperatures between about 0° C. and about 60° C., preferably between about 5° C. and about 35° C.

The chiral substituted cyclopentenone synthons obtained pursuant to the method of the present invention are useful in the syntheses of prostaglandins (PGs) such as $PGE_1$, $PGE_2$, and $PGF_{2\alpha}$ and their analogues and derivatives. For example, prostaglandin E1 ($PGE_1$) (FIG. 3) is synthesized from key intermediates (II) (FIG. 2) and (IV) (FIG. 1) which are isolated from crude lipase resolved mixtures, in high yields and purity.

The key intermediate for the preparation of intermediate (II) (FIG. 2) is intermediate (I) (FIG. 2), the R-enantiomer which is enzymatically resolved from racemic intermediate (5) (FIG. 2) by treatment of the corresponding acetate derivative (8) (FIG. 2) with porcine pancreatic lipase and isolated according to the method of the present invention. The S alcohol is easily recovered, as the lithium bromide complex, by filtration. The filtrate contains the desired R isomer, hence avoiding the need for complicated purification procedures.

The method of the present invention also has general applicability for resolving racemic mixtures into optically pure intermediates which are useful as synthons in the synthesis of other pharmaceutical agents, besides eicosanoids. Non-limiting examples include beta-blockers such as isoproterenol and propranolol; antibiotics such as penicillin G, ampicillin, amoxicillin, cephalosporins, chloramphenicol, erythromycin, and tetracycline; vitamins such as folic acid; prostaglandins such as misoprostol and enisoprostol; progestins such as norgestrel and norethindrone; antihypertensive agents such as spironolactone and propranolol hydrochloride; corticosteroids such as cortisol and dexamethasone; and antiarrhythmic agents such as disopyramide phosphate.

It has been discovered that the lithium bromide complexes of pharmaceutical agents, e.g. $PGE_1$, are exceedingly stable and provide an effective means for enhancing the shelf life of pharmaceutical compositions containing such agents in complexed form. This new formulation can be used as a "galentic" formulation for all "oily" drugs such as prostaglandins, leukotrienes, eicosapentaenoic acids, lipoxins (e.g. LxA$_4$, LxA$_5$, LxB$_4$, and LxB$_5$) and fatty acids and their derivatives.

In another embodiment of the present invention, PGE$_1$ can be obtained from a PGE$_1$ ester having the formula:

wherein R is selected from the group consisting of hydrogen; alkyl of 1 to 6 carbon atoms; adamantyl; β-oxo-carbonyl; aryl; heteroaryl such as pyridine, quinoline, benzofuran, benzothiophene and thiophene; and heterocyclic such as tetrahydropyran, tetrahydrofuran, and dioxane, by a method comprising contacting said PGE$_1$ ester with an amount of lipase, in the presence of organic solvent, effective for hydrolyzing the ester into PGE$_1$. The lipase catalyzes the selective hydrolysis of the ester and results in a highly pure PGE$_1$.

In practicing the invention, any one of the aforementioned lipases can be employed in the enzymatic hydrolysis, however, porcine pancreatic lipase is preferred.

The enzymatic reaction is conducted at a temperature between about 0° C. and about 40° C., preferably about 25° C., for a time period ranging between about 1 hour and about 24 hours, preferably about 6 hours. The mixture is stirred throughout this period by conventional means which include mechanical stirring and shaking.

The amount of lipase used per mole of PGE$_1$ ester ranges between about 1% and about 100%, preferably about 5% and about 50%.

Suitable, but non-limiting, examples of organic solvents for use in the reaction include THF, alcohols, and dioxane in the presence of water. A preferred organic solvent is THF.

Thereafter, the PGE$_1$ is separated from the enzyme suspension by conventional techniques which include filtration, centrifugation, and decantation.

It has been further discovered that chiral alcohols of halovinyl ketones (A) and alkynyl ketones (B), useful in the synthesis of eicosanoids, are obtained by reducing a compound of the formula:

wherein R$_9$ and R$_{10}$ are independently selected from the group consisting of hydrogen; alkyl, alkenyl or alkynyl having 2 to 10 carbon atoms; adamantyl; and R$_3$R$_4$R$_5$Y wherein Y=Si or Sn and wherein R$_3$, R$_4$ and R$_5$ are independently selected from the group consisting of methyl, ethyl, isopropyl, t-butyl and phenyl; and X is selected from the group consisting of hydrogen, iodine, chloride, bromide, fluoride, and R$_6$R$_7$R$_8$Y wherein Y=Si or Sn and wherein R$_6$, R$_7$ and R$_8$ are independently selected from the group consisting of methyl, ethyl, isopropyl, t-butyl and phenyl, with a chiral boronic catalyst, in the presence of organic solvent.

Figure 1:
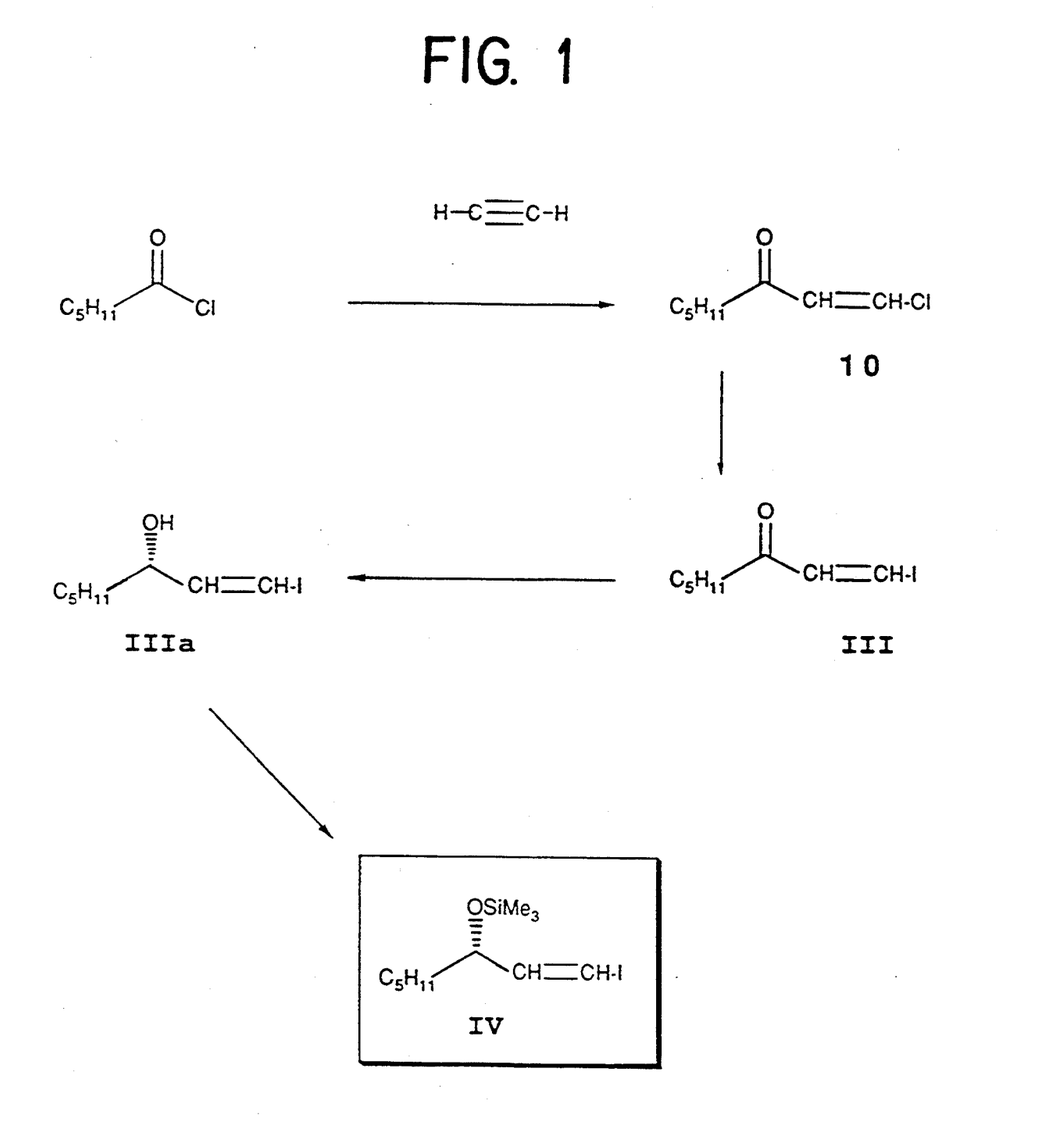
FIG. 1 illustrates the synthesis of chiral iodinated substituted allylic alcohols, e.g. 1-iodo-hepten-1-en-3-ol (IIIa), and its trimethylsilyl protected derivative (IV).

The chiral alcohols produced by the reduction reaction of the present invention are useful intermediates for the syntheses of prostaglandins (PGs) such as PGE$_1$, PGE$_2$, and PGF$_{2\alpha}$; leukotrienes (LTs) such as LTB$_4$, LTB$_5$, HETEs and diHETEs; thromboxanes (Tx) such as TxA$_2$, TxB$_2$; and lipoxins such as LxA$_4$, LxA$_5$, LxB$_4$, LxB$_5$ and analogues and derivatives of the foregoing. FIG. 1 illustrates the preparation of (S)1-iodo-hepten-1-en-3-ol from 1-iodo-hepten-1-en-3-one using a N-butylboronic complex of D(−) prolinol as reduction catalyst.

In practicing the invention, the chiral boronic catalyst is slowly added, dropwise, to a solution containing halovinyl ketone or alkynyl ketone. In general, the molar ratio of halovinyl ketone or alkynyl ketone to chiral boronic catalyst ranges between about 1:0.01 and 1:1, preferably between about 1:0.05 and about 1:0.20. To ensure high values of enantiomeric excess, the rate of addition should be generally between about 1 hour and about 24 hours, preferably between about 6 hours and about 12 hours.

The reduction reaction is conducted, under an inert atmosphere of nitrogen or argon, at a temperature between about −100° C. and about −60° C., preferably about −70° C., for a time period ranging between about 10 hours and about 24 hours, preferably about 12 hours. The reaction is stirred throughout this period by conventional means which include magnetic stirring and mechanical.

Suitable, but non-limiting, examples of chiral boronic catalyst for use in practicing the invention and a method for their preparation have been described in U.S. Pat. No. 4,943,635 which is incorporated by reference in its entirety. Particularly preferred boronic catalysts include N-butylboronic, methylboronic, and phenylboronic complexes of optically active diphenyl D(−) or L(+) prolinols. Chiral boronic catalysts are commercially available from a number of sources such as Lancaster Synthesis (Windham, N.H., USA).

Suitable, but non-limiting, examples of organic solvents for use in the reaction includes toluene, THF and ether. These solvents must be anhydrous and procedures for drying such solvents are known in the art. A preferred organic solvent for use in this invention is toluene.

In the Examples below, Examples 1–16 illustrate the total organic synthesis of PGE$_1$ pursuant to the methods of the present invention; Examples 17 and 18 are directed to the biological effects of PGE$_1$ produced in accordance with the methods of the present invention compared with commercially available PGE$_1$, and Example 19 shows the enhanced stability of PGE$_1$ produced in accordance with the methods of the present invention. The specific working examples are intended to illustrate practice of the present invention without limiting its scope.

EXAMPLE 1

Figure 2:
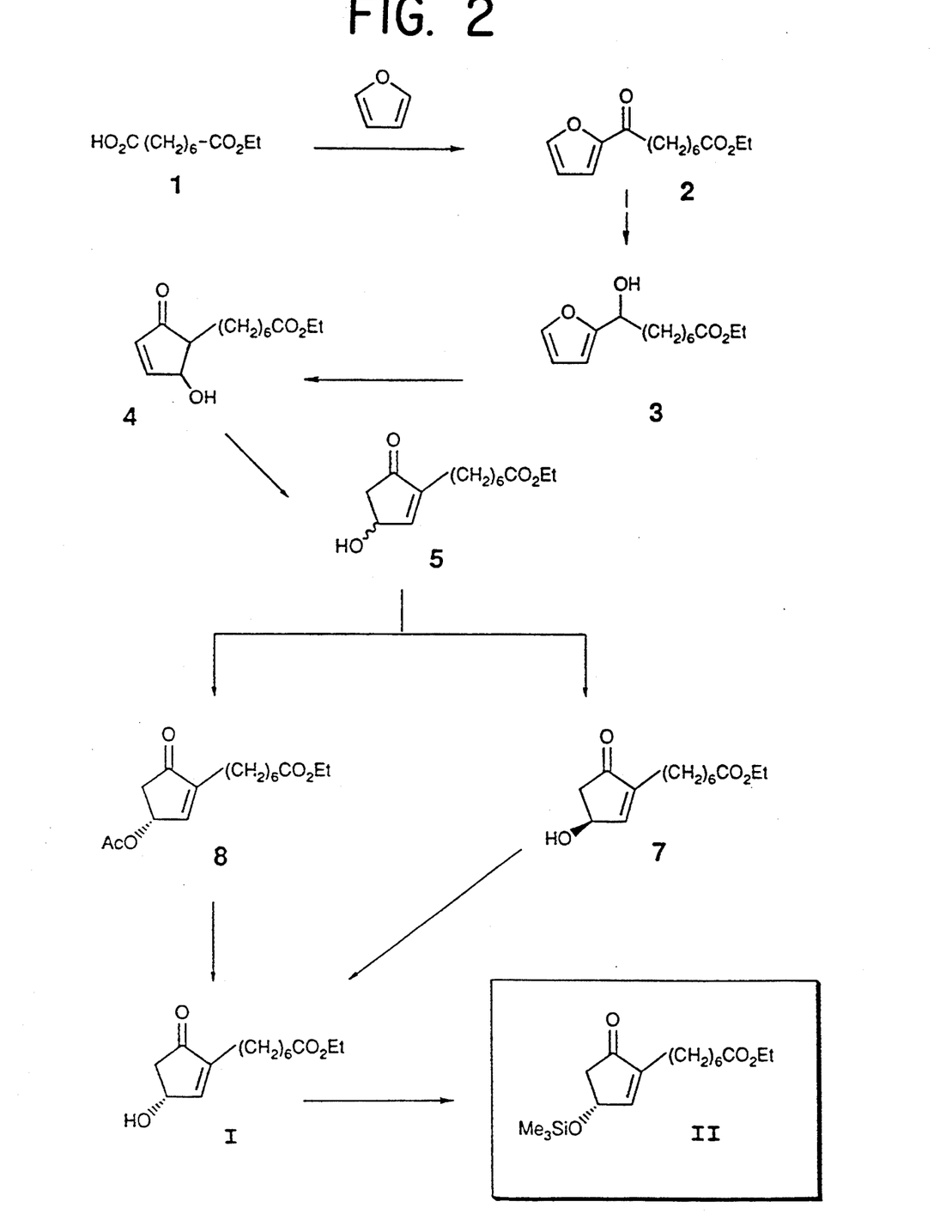
FIG. 2 illustrates the present method for enzymatically resolving and isolating chiral intermediate (II), a precursor to PGE$_1$-Et and PGE$_1$.

Synthesis of Intermediate 1 (FIG. 2)

To a 580 ml solution of benzene and ethanol (2:0.9 v/v) contained in a 2000 ml flask fitted with a Dean-Stark trap was added 200 grams (1.148 moles) suberic acid and 1 ml concentrated sulfuric acid. The solution was refluxed for 13 hours until the cessation of water distillation. The solution was cooled and solvent removed under reduced pressure. The residue was dissolved in diethyl ether and the solution was washed with saturated NaHCO$_3$ solution and dried (NaSO$_4$).

The product was distilled under vacuum (1 mm Hg) at 25° C. Yield of the diester was quantitative.

264.3 grams (1.15 moles) of the diester was reacted with 850 ml 85% ethanolic KOH solution at 0° C. for 12 hours. The solution was stirred for 6 hours at 20° C. Thereafter, the ethanol solvent was removed under reduced pressure and the residue was dissolved in 500 ml water. The solution was extracted four times with 300 ml portions of diethyl ether. The pooled extracts were dried (NaSO$_4$) and the solvent was removed under reduced pressure. The residue was acidified with aqueous 10% HCl solution and the mixture was extracted four times with 200 ml portions of methylene chloride to dissolve the desired monoester (1) from the diacid. Thereafter, the pooled extracts were dried (Na$_2$SO$_4$) evaporated and distilled. The yield of the reaction was 85%. K$_{p10}$ 175°–185° C.

$^1$H NMR (in ppm related to CDCl$_3$): 9.80 broad (1H), 4.10 quartet (2H), 2.30 two triplets (4H), 1.60 multiplet (4H), 1.35 multiplet (4H) and 1.25 triplet (3H).

$^{13}$C-NMR (in ppm relative to CDCl$_3$): 176.9, 173.8, 60.2, 34.2, 33.9, 28.7, 28.6, 24.7, 24.5 and 14.2.

EXAMPLE 2

Synthesis of Intermediate 2 (FIG. 2)

To a 60 ml carbon tetrachloride solution, 10.21 grams (0.05 moles) of monoester and 5.11 grams (0.0505 moles) of triethylamine was added. The solution stirred at 0° C. Thereafter, 5.71 grams (0.0505 moles) of chloroacetyl chloride was added dropwise. At the completion of addition, the reaction mixture was stirred at room temperature for three hours and was then filtered under reduced pressure to remove precipitated salts. To the filtrate was added 5.11 grams (0.075 moles) of furane and 0.71 grams (0.005 moles) of boron trifluoride-diethyl ether and the resulting mixture was heated at 40° C. for four hours. The solution was then cooled and washed successively with 50 ml of water, 50 ml of 5% sodium bicarbonate, 50 ml of water and dried (NaSO$_4$). The yield was 66.7% (Compound 2) after vacuum distillation (0.01 mmHg). K$_{P0.2}$ 136°–139° C.

$^1$H NMR (in ppm relative to CDCl$_3$): 7.55 doublet (1H), 7.20 doublet (1H), 6.50 double doublet (1H), 4.10 quartet (2H), 2.80 quartet (2H), 2.30 triplet (2H), 1.70 multiplet (4H), 1.35 multiplet (4H) and 1.25 (3H).

EXAMPLE 3

Synthesis of Intermediate 3 (FIG. 2)

72.3 grams (0.286 moles) of Compound 2 was dissolved in 800 ml of ethanol. 10.4 grams (0.27 moles) of sodium borohydride (in excess) was added in small portions until the starting material disappeared on TLC (1:1 hexane/ethyl acetate solvent system). The resulting product (Compound 3, 80.3 grams, yield=96%) contained traces of ethanol.

$^1$H-NMR (CDCl$_3$): 7.33 (doublet of doublets, 1H); 6.32 (1H); 6.22 (broad, 1H); 5.255 (m, 2H); 4.70 (quartet, 2H); 2.45-2.05 (m, 7H); 7.35 (m, 4H); 7.25 (t, 3H)

$^{13}$C-NMR (CDCl$_3$): 173.6; 156.6; 141.7; 130.1; 128.3; 110.0; 105.6; 66.8; 60.2; 35.2; 33.9; 23.2; 22.7; 14.3

EXAMPLE 4

Synthesis of Intermediate 4 (FIG. 2)

This intermediate was prepared in accordance with J. H. Dygos et al. (1991) *J. Org. Chem.*, Vol. 56, page 2549.

To 1.25 l of dioxane was added 144.6 grams (0.6 moles) of Compound 3 at 25° C. The solution was then added dropwise (with stirring) to a one liter water solution containing 320 grams (2.35 moles) of zinc chloride at 25° C. for one hour. The reaction mixture was then refluxed for 24 hours, then cooled to room temperature. The dioxane was removed under reduced pressure and the residue was acidified to pH 1.0 with an aqueous 15% HCl solution and extracted twice with 500 ml portions of ethyl acetate. The pooled extract was then washed successively with 150 ml saturated sodium bicarbonate (3 times), once with 200 ml brine, then dried (sodium sulfate). Solvent was removed under reduced pressure to afford 115 grams (80% yield).

$^1$H-NMR (CDCl$_3$): 7.52 (doublet of doublets, 1H); 6.20 (doublet of doublets 1H); 5.25-5.55 (m, 2H); 4.71 (m, 1H); 4.10 (quartet 2H); 3.73 (d 1H); 2.16-2.58 (m, 7H); 1.95 (m, 1H); 1.50 (m, 7H); 1.25 (t, 3H).

C-NMR (CDCl$_3$): 208.2; 173.8; 162.4; 133.5; 130.1; 128.3; 76.3; 66.8; 60.2; 33.8; 28.4; 24.8; 22.5; and 14.3

EXAMPLE 5

Synthesis of Ethyl-7-(3-hydroxy-5-oxo-1-cyclopen-1-yl)-heptanoate) (5) (FIG. 2)

Intermediate 5 was prepared in accordance with the procedure described in Novak et al. (1979) *Acta Chem. Acad. Sci. Hungarica*, Vol. 102(1), Pages 91–100.

A solution containing anhydrous chloral (4 grams, 27 mmoles), 2'-hydroxycyclopentenone (4) (120 grams, 4.65 mmoles) and triethylamine (43 grams, 0.31 moles) in dry toluene (one liter) was heated to 65° C. for six hours. After cooling to 20° C., the mixture was filtered through a 4 cm bed of silica gel and the solvent was removed under reduced pressure (2 mm Hg) to afford a yellow oil (120 grams, 95% yield).

EXAMPLE 6

Conversion of Intermediate 5 into 7 and 8 (FIG. 2)

Resolution of Intermediate 5 was performed in accordance to Babiack et al. (1990) *J. Org. Chem.*, Vol. 55, Pages 3377-3381.

A mixture of 120 grams (0.45 moles) of ethyl 7-(3-hydroxy-5-oxo-1-cyclopenten-1-yl)-4(-Z)-heptenoate), intermediate (5), 120 grams of porcine pancreatic lipase (available from Sigma Co., St. Louis, Mo. U.S.A.) and 1.5 liters of distilled vinyl acetate were vigorously stirred at room temperature for 7 days. The crude mixture was then filtered through celite and concentrated under reduced pressure (2 mm Hg). The resulting residue is dissolved in 100 ml toluene which was then added to a slurry containing 700 grams of lithium bromide in 700 ml hexane and 1.2 liter of toluene. The mixture stirred for two hours at 20° C. during which time the lithium bromide complex of intermediate (7) is formed. The lithium bromide complex is then filtered and the remaining filtrate contained intermediate (8). Cleavage of the lithium bromide complex was performed as follows: The lithium bromide complex was dissolved in ethyl acetate/water (ratio 4:1) and stirred at 0° C. for 1 hour and 25° C. for 2 hours. Thereafter, the ethyl acetate phase was separated. The water phase was washed twice with 300 ml portions of ethyl acetate and the ethylacetate phases were combined and washed with 100 ml H$_2$O, 100 ml NaCl solution and dried (Na$_2$SO$_4$). Evaporation of solvent gave 60 grams of alcohol (7).

Intermediate (7) isolated as described was then subjected to a Mitsunobu inversion (Example 7). Purification of Compound (8) was performed as follows: evaporation of the solvent afforded 58 grams (49% yield) of purified intermediate (8).

EXAMPLE 7

Mitsunobu Inversion of Intermediate 7 (FIG. 2)

The reaction conditions described in this Example are the same as found in (1990) *J. Org. Chem.*, Vol. 55, pages 3377–3381.

To a solution of THF (450 ml) and formic acid (10 ml) was added 33.7 grams (132.51 mmoles) of Compound (5) (beta) and 69.51 grams (265.01 mmoles) of triphenylphosphine and the solution was cooled down to −5° C. Thereafter, 41.73 ml (265.01 mmoles) of diethylazodicarboxylate was added and the temperature was increased to 15° C. Thereafter the reaction mixture was warmed to room temperature and was stirred overnight. The solvent was then evaporated and the oily residue was taken up in diethyl ether (600 ml) and stirred for 30 minutes. The mixture was filtered and 300 ml of pentane was added. The solution was dried over sodium sulfate, filtered and evaporated to afford 30 grams (93% yield) of the formate ester derivative, which was used directly as described in Example 8 to provide intermediate (I) from the acetate.

EXAMPLE 8

Synthesis of Intermediate I (FIG. 2)

Intermediate (I) was prepared in accordance with Babiack et al. (1990) *J. Org. Chem.*, Vol. 55, Pages 3377–3381.

A stock solution of 0.5M guanidine in ethanol was prepared by adding 1.78 grams (77.4 mmoles) of hexane washed sodium spheres to ice-cooled ethanol (154 ml) under an argon atmosphere. When all the sodium had reacted, 14.2 grams (79.0 mmoles) of guanidine carbonate was added. The solution was stirred at room temperature for 25 minutes, and the mixture was allowed to stand to settle out precipitated salts. In a separate flask was added 128 grams (0.45 mmoles) of (R)-acetate of (I) in 500 ml of absolute ethanol under argon. This was cooled to 0° C. in an ice bath, and to it was added via syringe 100 ml of 0.5 molar guanidine in ethanol prepared above, over approximately 5 minutes. This mixture was stirred at approximately 10° C. for 5 minutes. TLC (80% ethyl acetate and hexane on silica gel) showed complete consumption of acetate. To the reaction mixture was then added 2.86 ml (3.00 grams, 50.00 mmoles) of glacial acetic acid to neutralize the quanidine. After the mixture was stirred for 5 minutes, solvent was removed at reduced pressure to give a thick slurry. The residue was partitioned between 100 ml of water and 500 ml of ethyl acetate. The aqueous layer was further extracted with two 50 ml portions of ethyl acetate. The combined organic layers were washed with two 50 ml portions of water and 50 ml of brine and dried over sodium sulfate. Removal of solvent at reduced pressure gave a (93% yield) of a yellow oil.

EXAMPLE 9

Synthesis of Ethyl-7(5-oxo-3R[(trimethylsilyl)oxy-1-cyclopenten-1-y]-heptanoate (II) FIG. 2)

Preparation of Intermediate (II) was performed in accordance with (1991) *J. Org. Chem.*, Vol. 56(7), Pages 2549–2552 and (1990) *J. Org. chem.*, Vol. 55, pages 3377–3381.

To a 800 ml solution of THF containing 254 grams Compound (I) (1 mole), and 120 grams (1.2 moles) triethylamine at 0° C. was added 120 grams (1.1 moles) of trimethyl silylchloride dropwise over a period of one hour. The solution stirred for 3 hours at 20° C. until the reaction was completed as determined by TLC. Thereafter, the reaction mixture was filtered to remove white precipitate and the solvent was removed by evaporation. The residue was dissolved in 1000 ml pentane and filtered through celite. Evaporation of the solvent afforded 310 grams (95% yield) of material in >95% purity as determined by $^1$H-NMR, $^{13}$C-NMR and TLC.

$^1$H-NMR (CDCl$_3$): 7.08 (1H); 4.88 (1H); 4.13 (2H); 3.74 (1H); 2.2 (5H) , 1.80–1.0 (11H); 0.85 (3H); 0.15 (9H)

$^{13}$C-NMR (CDCl$_3$): 206; 173; 156; 147; 68; 60; 45; 34; 28.9; 28.9; 27; 24.8; 24.3; 14; 6.6; 6.5; 5.7; 4.6

EXAMPLE 10

Synthesis of Intermediate 10 (FIG. 1)

To a slurry of 233.5 grams (1.75 moles) of aluminum chloride in 390 ml of carbon tetrachloride acetylene gas was added until saturation was reached. The solution was cooled in an ice bath. Thereafter, 201.9 grams (1.50 moles) of hexanoyl chloride was added over 20 minutes. At the completion of the addition, acetylene was bubbled into the mixture at the absorption rate for a period of about three hours. The mixture was then poured into a beaker containing 1700 grams of crushed ice and 720 ml of saturated brine. The organic phase was separated and the pooled organic phase was neutralized with sodium bicarbonate and washed with saturated brine, dried (sodium sulfate) and evaporated. The residual crude oil was combined with 10 grams of hydroquinone and distilled to yield a colorless oil, B. pt. 51° to 52° C. (0.1 torr), 195 grams (1.2 moles), 70% yield after distillation.

$^1$H NMR (in ppm relative to CDCl$_3$): 7.3, (doublet, 1H), 6.5, (doublet, 1H); 2.5 (triplet, 2H); 1.6 (multiplet, 2H); 1.3 (multiplet, 4H); and 0.9 (triplet, 3H) .

$^{13}$C NMR (in ppm relative to CDCl$_3$): 197.5, 136.3, 132.3, 41.3, 31.3, 23.5, 22.4, 10.0.

EXAMPLE 11

Synthesis of Intermediate III (FIG. 1)

To a 500 ml acetone solution was added 195 grams of (1.215 moles) of Compound 10 and 265.9 grams (1.776 moles) of sodium iodide plus 150 mg of AlCl$_3$. The solution was stirred and refluxed for 24 hours. Thereafter, the mixture was cooled, filtered and the solvent removed by reduced pressure. The residue was dissolved in ether and the solution was washed with sodium sulfite, dried (Na$_2$SO$_4$) and concentrated to give 305 grams (97.7% yield) of Compound (III).

$^1$H-NMR (CDCl$_3$): 7.9 (d, 1H); 7.15 (d, 1H); 2.5 (t, 2H); 1.8–1.1 (m, 6H); 0.89 (t, 3H) $^{13}$C-NMR (CDCl$_3$): 197.6; 144.5; 98.6; 40.4; 31.3; 23.4; 22.4; 13.9

Example 12

Synthesis of Intermediate IIIa (FIG. 1)

One mole of (III) was added to 0.02 mol of Corey catalyst, the N-butylboronic complex of diphenyl D(−) prolinol (Lancaster Synthesis, Inc., Windham, N.H., USA) in 800 ml toluene and the solution (totally dry) was cooled to −70° C. under argon. To this cold solution was added 500 ml of a 4M catecholborane solution in toluene (Aldrich Chemicals, St. Louis, Mo.) over twelve hours. After 24 hours at −70° C. the reaction was stopped by dropwise CH$_2$OH to destroy excess borane and the resultant solution was warmed to 0° C. over one hour. The solution was extracted six times with 200 ml aliquots of 4N NaOH to remove catechol, extracted twice with 100 ml aliquots of 10% HCl washed once with brine, dried (Na$_2$SO$_4$), and rotoraped down to afford IIIa in 95% crude yield with an enantiomeric in excess (ee) of greater than 98% as determined by $^{13}$H-NMR and $^{13}$C-NMR (as the Mosher ester).

$^1$H-NMR (CDCl$^3$): 6.5 (q, 1H); 6.25 (d, 1H); 4.0 (q, 1H); 1.80–1.00 (m, 9H); 0.80 (t, 3H)

$^{13}$C-NMR (CDCl$_3$): 148.6; 77.1; 74.7; 36.5; 31.6; 24.8; 22.5; 14.0

Example 13

Sharpless Kinetic resolution of IIIa (FIG. 1)

The compound described in Example 12 was treated according to *J. Org. Chem.*, Vol. 55(19), Page 5332 using D(−) diisopropyl tartrate.

40 ml of dichloromethane was dissolved 11.4 mmoles of titanium tetraisopropoxide and 12.8 mmoles of D(−) diisopropyl tartrate. To the solution (cooled to −20° C.) was added 20 ml of dichloromethane solution containing 10 grams (36 mmoles) of Compound (III) under an argon atmosphere, followed by stirring for 15 minutes. Thereafter, 632 ml of a dichloromethane solution containing 273 mmoles of t-butyl hydroperoxide was added, followed by stirring for 40 hours at −20° C. With the addition of 3 ml of dimethylsulfide, stirring was continued for 10 minutes. To the resulting solution was added 8 ml of 10% aqueous solution of tartaric acid, 150 ml of diethyl ether and 3 grams of sodium fluoride and 10 grams of celite, followed by stirring at room temperature. The reaction mixture was filtered and the residue was washed with 100 ml of diethyl ether. The washings were combined with the filtrate. The filtrate was distilled under reduced pressure to remove the solvent. Thus there was obtained 16 grams of a crude product which was purified by silica gel chromatography to afford 8 grams (80% overall yield) of the desired compound, with an ee>99.9%.

EXAMPLE 14

Synthesis of (3S)-(trimethylsilyl) oxy-trans-1-octenyl iodide IV (FIG. 1)

To a 200 ml DMF was added 57 grams (0.2245 moles) of Compound (IIIa), 34.1 grams (0.34 moles) of triethylamine and 30.6 grams (2 equiv.) of imidazole. The solution stirred at 0°–5° C. and 36.58 grams (0.336 moles) of trimethylsilylchloride was added dropwise. The solution stirred for 4 hours at 20° C. until the reaction reached completion. The reaction mixture was quenched and diluted with hexane and washed twice with water and sodium chloride. The solution was dried (Na$_2$SO$_4$) and evaporated to afford 73.2 grams (100% yield).

$^1$H-NMR (CDCl$_3$): 6.5 (d of d, 1H); 6.2 (d, 1H); 4.05 (q, 1H); 1.7–1.1 (m, 8H); 0.9 (t, 3H); 0.1 (s, 9H)

$^{13}$C-NMR (CDCl$_3$): 149.11; 75.65; 75.08; 37.33; 31.63; 24.82; 22.54; 14.01; 0.11

$\alpha_D$ (20° C.) = −27.4 (CH$_2$Cl$_2$)

EXAMPLE 15

Figure 3:
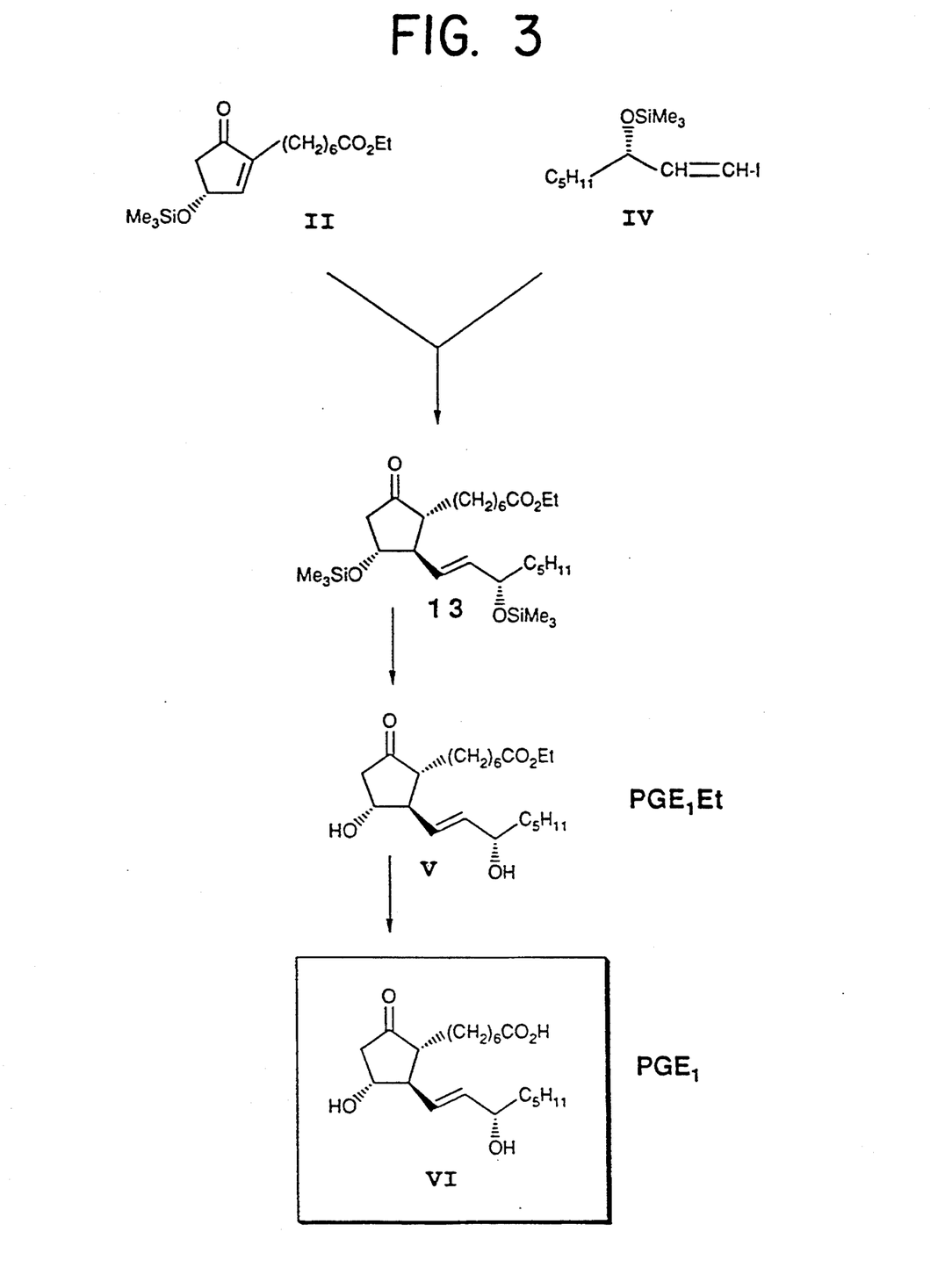
FIG. 3 illustrates conjugate addition of chiral intermediates IV and II to produce PGE$_1$-Et and PGE$_1$.

(−)-Ethyl 11-alpha, 15(S)-dihydroxy-9-oxoprosta-4-(Z),13(E)-dien-1-oate (PGE$_1$-Et, V) (FIG. 3)

Intermediate (V) was prepared in accordance with Kobayashi et al. (1990) *J. Org. Chem.*, Vol. 55, Pages 5324–5335.

A solution of intermediate (IV) (FIG. 3) (300 g, 0.92 mol) in Et$_2$O (1 liter) in a flamed-dried flask was degassed under vacuum and placed under argon by releasing the vacuum with argon. The solution was cooled to −70° C., and a solution of 1.6M n-butyllithium in hexane (575 ml, 0.94 mol) was added. The resulting solution was stirred at −70° C. for 2 hours.

CuCN (82.4 g, 0.92 mol) was placed in a second flame dried flask. Diethyl ether (500 ml) was added, and the mixture was cooled at −70° C. A solution of 1.39M methyllithium in ether (657 ml, 0.92 mol) was added, and the mixture was warmed to 0° C. for 45 minutes. The mixture was cooled to −70° C., and the previous vinyllithium solution was added via cannula. The mixture was slowly warmed to −30° C. for 20 minutes and cooled to −70° C. A solution of intermediate (II) (FIG. 3) (150 g, 0.46 mol) in Et$_2$O (500 ml) was added. After 20 minutes, the reaction mixture was poured into a mixture of 9/1 saturated aqueous NH$_4$Cl/NH$_4$OH solution (2000 ml) layered with Et$_2$O (2 liter). The mixture was vigorously stirred for 30 minutes, and the layers were separated. The aqueous phase was extracted twice with Et$_2$O (2000 ml total), and the combined organic phases were washed twice with a mixture of 9/1 saturated aqueous NH$_4$Cl/NH$_4$OH solution (500 ml total). The organic phase was dried (Na$_2$SO$_4$), filtered, and concentrated in vacuo.

Figure 4:
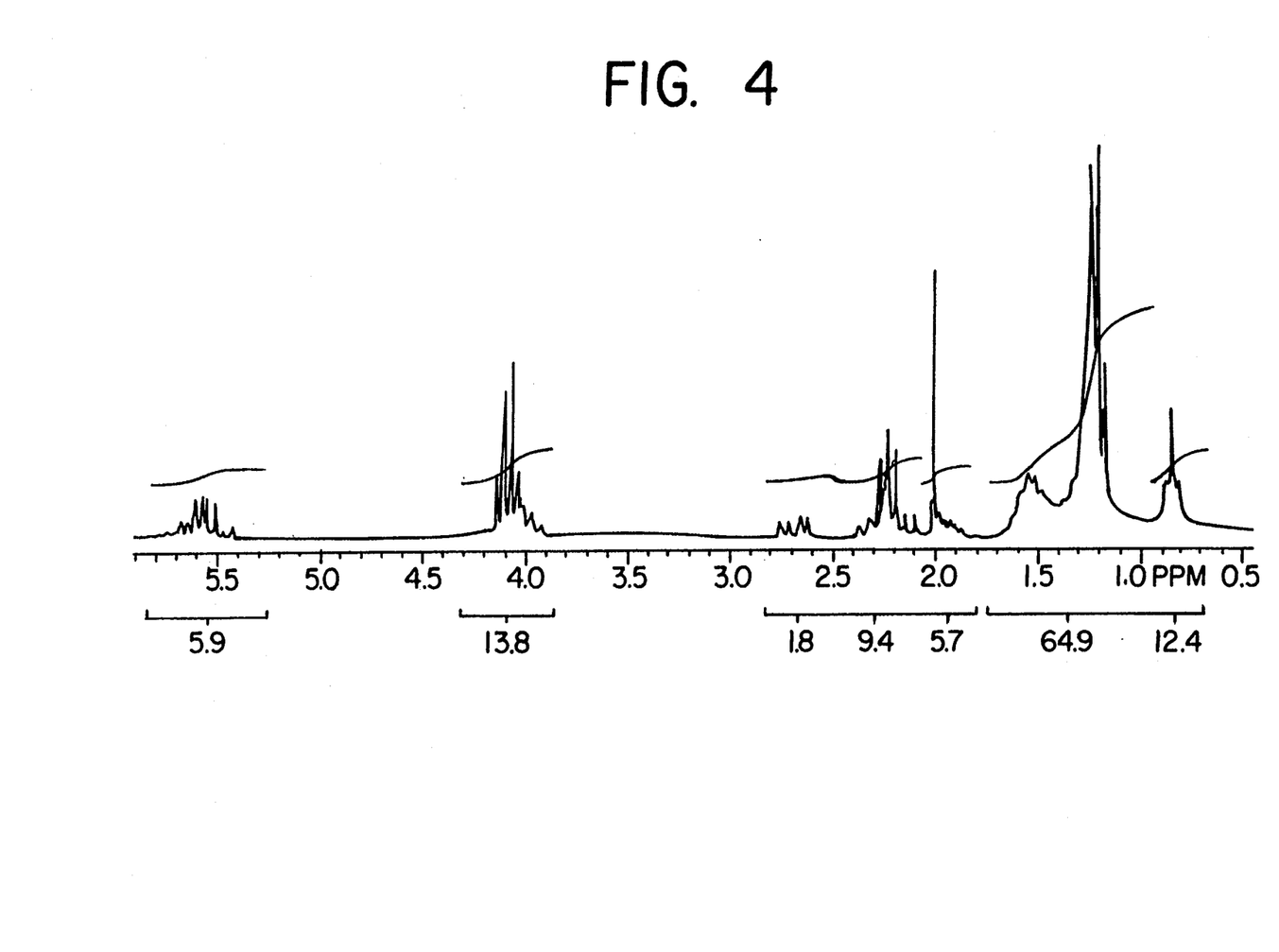
FIG. 4 is a 200 MHz $^1$H-NMR spectrum of PGE$_1$-Et. This spectrum was obtained from a Varian Gemini 200 instrument (Varian, Palo Alto, Calif.) using CDCl$_3$ as solvent.
Figure 5:
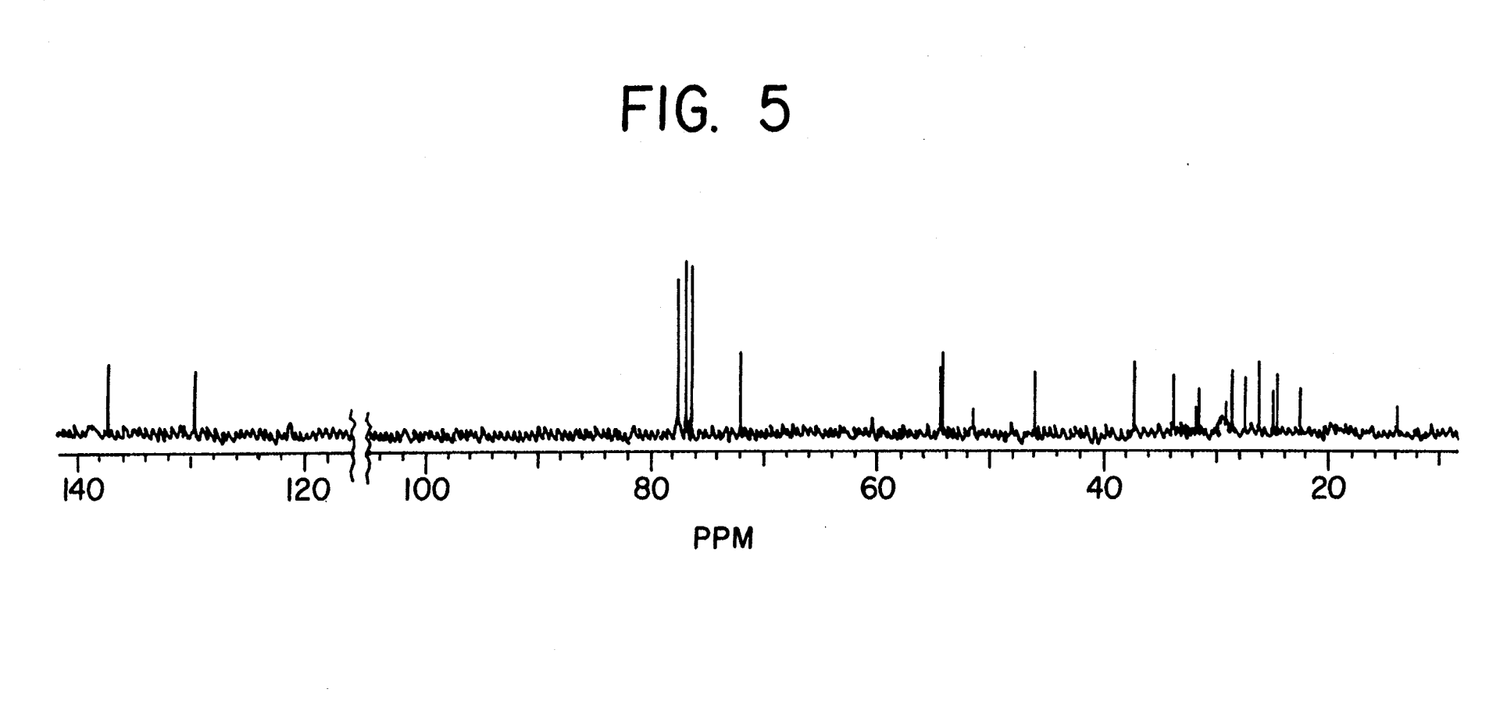
FIG. 5 is a 200 MHz $^{13}$C-NMR spectrum of PGE$_1$-Et. The spectrum was obtained under identical conditions as described in FIG. 4.

The crude intermediate (13) was dissolved in a solution of acetone (2000 ml) and water (400 ml). The solution was treated with pyridinium p-toluenesulfonate (PPTS) (2 g) and stirred at room temperature for four hours. The solvent was then removed in vacuo, and the residue was partitioned between ethyl acetate (2 liter) and saturated NaCl solution (400 ml). The layers were separated, and the aqueous phase was extracted twice with EtOAc (1000 ml total). The combined organic phase was washed with saturated NaCl solution (200 ml), dried (Na$_2$SO$_4$), and filtered. The filtrate was concentrated in vacuo to give 270 g of a product mixture containing crude (10), which was purified by dissolving in acetonitrile and extracting impurities with hexane and give PGE$_1$ ethyl ester. The solvent was removed in vacuo to give 145 grams of PGE$_1$ ethyl ester (V) (FIG. 3) (85% yield based on II). FIGS. 4 and 5 correspond to the $^1$H-NMR and $^{13}$C-NMR spectra, respectively, of PGE$_1$ ethyl ester.

NMR Spectral data:

$^1$H NMR (CDCl$_3$) δ: 5.9, 13.8, 1.8, 9.4, 5.7, 64.9, 12.4;

EXAMPLE 16

Synthesis of $PGE_1$ (VI)

The reaction conditions used in this Example are a modification of the conditions described in C. Sih (1972) *J. Amer. Chem. Soc.*, Vol. 94, page 3643. The differences are that porcine pancreatic lipase is used instead of baker's yeast, and THF is employed as solvent. Additionally, solid $KHSO_4$ is used in the extraction step instead of water. The present extraction process avoids the use of large quantities of ethyl acetate and the loss of $PGE_1$ due to its facile solubility in water.

To 1.2 g porcine pancreatic lipase (Type VI-S, Sigma Chemical Co., St. Louis, Mo.), 100 mg NaCl and 30 mg $CaCl_2$ in 300 ml of water was added 20 g of $PGE_1$ ethylester (VI) in 50 ml THF. The pH of the solution was maintained at 7.05–7.10 using a titroprocessor with 0.1N NaOH. After 30 minutes without pH changes, the solvent was removed under vacuum (2 mmHg) and solid $KHSO_4$ (100 g) and NaCl (200 g) were added to the residue and $PGE_1$ was extracted with 1000 ml ethyl acetate. The crude product was recrystallized from ethyl acetate/hexane (ratio 2:1) to give (−)$PGE_1$ >95% yield. The recrystallized $PGE_1$ had a melting point (m.pt.) range of 117°–118° C. (reported m.pt. 115°–116° C.)

EXAMPLE 17

In Vivo Evaluation of $PGE_1$ on Arterial Blood Pressure

Evaluations of $PGE_1$, prepared in accordance with the present invention, on blood pressure regulation in genetically hypertensive rats were performed in vivo with infusion of $PGE_1$ intravenously (IV) in conscious spontaneously hypertensive rats (SHR) (12 male rats, 300–450 grams) as well as normal weight matched male Sprague Daweley rats. $PGE_1$ were dissolved in pure ethanol (10 mg/ml) and diluted with 0.9% NaCl (saline) before infusion to rats. $PGE_1$ solutions were administrated at the dose of 10 μg, 30 μg, 100 μg, and 300 μg/kg intravenously into SHR and normal rats as described in Lin et al. (1990) *Biochem. Biophy. Res. Comm.*, Vol. 167(3), Pages 977–981. The blood pressure lowering effect was compared to the $PGE_1$ obtained from ONO Pharmaceutical Company, Japan and Upjohn, USA.

The results (not shown) demonstrate that the $PGE_1$ obtained from the present synthesis is biologically active and produced a dose dependent blood pressure lowering effect in normal as well as genetically hypertensive rats. The hypotensive effect of the $PGE_1$, at a wide dose range obtained from the present synthesis were identical to those produced by the $PGE_1$ from ONO and Upjohn.

EXAMPLE 18

In Vitro Evaluation of PGE on Platelet Aggregation

In vitro evaluations of $PGE_1$, produced in accordance with the present invention, on platelet aggregation were performed using platelet rich plasma (PRP) obtained from human blood as described by Wong et al. (1979) *Euro. J. Pharm.*, Vol. 60, Pages 245–248. Biological assays were performed with 0.5 ml aliquot of PRP stirred at 1,200 rpm at 37° C. in a dual channel Payton aggregation module and transcribed on a linear recorder (Payton Associates, Buffalo, N.Y.). The concentrations of $PGE_1$ (1, 5, and 10 nanograms) obtained from the present synthesis was compared to the similar dose range of $PGE_1$ obtained from ONO and Upjohn required to inhibit platelet aggregation induced by ADP (6 micromolar). $PGE_1$ was stored in dry acetone (1 mg/ml) at −25° C. and diluted with TRIS buffer (50 mM, pH 8.8) before use.

It was found that the $PGE_1$ obtained pursuant to the present synthesis had the identical potency in inhibiting platelet aggregation as the $PGE_1$ obtained from ONO and Upjohn.

EXAMPLE 19

Galentic Formulation of Misoprostol

Lithium bromide complexes of pharmaceutical agents, e.g misoprostol (Cytotec ®, available from G. D. Searle, Chicago, Ill., USA) and other prostaglandins, provide an effective means for enhancing the shelf life of pharmaceutical agents containing these materials. In this example, a galentic formulation of misoprostol as a lithium bromide complex is described.

To a 50 ml toluene solution containing 900 mg LiBr is added a 5 ml toluene solution containing 100 mg misoprostol with stirring. The mixture is stirred for 2 hours at room temperature, then concentrated and dried under vacuum to afford 1 gram misoprostol-LiBr complex as a powder. The lithium complex can be incorporated into tablets as a powder by simply mixing conventional ingredients with the complex.

EXAMPLE 20

Misoprostol Formulation and Evaluation of Stability

Tablets containing the misoprostol-LiBr complex are prepared by conventional methods and contain the following:

| Ingredient | Amount |
| --- | --- |
| LiBr | 2 mg |
| Misoprostol | 200 mg |
| Hydroxypropyl methyl cellulose | 66.3 mg |
| Microcrystalline cellulose | 66.3 mg |
| Sodium starch glycolyte | 66.3 mg |

Tablets and misoprostol oil (as control) are stored for one year at room temperature and in air. At three month intervals, a tablet is dissolved in water and samples are withdrawn and analyzed by HPLC and GC. The amount of misoprostol remaining in the tablet is expected to be unchanged while misoprostol oil shows substantial decomposition products.

What is claimed is:

1. A method for resolving a compound selected from the group consisting of:

wherein X is selected from the group consisting of alkyl, alkenyl and alkynyl groups having 2 to 10 carbon atoms; and R is selected from the group consisting of —$CH_2OR_1$ and —$CO_2R_2$ wherein $R_1$ is selected from the group consisting of hydrogen, alkyl of 1 to 6 carbon atoms, ethoxyethyl, adamantyl, aryl, heteroaryl, and heterocyclic, and $R_2$ is alkyl of 1 to 6 carbon atoms, without employing chromatography, said method comprising the steps of:
(a) contacting said compound with an effective amount of a lipase and an effective amount of an acylating reagent so as to form the corresponding S alcohol and R acetate;
(b) treating said S alcohol with a lithium salt in an anhydrous solvent so as to form a lithium salt complex; and
(c) recovering said lithium salt complex.

2. The method according to claim 1, wherein said lipase is porcine pancreatic lipase.

3. The method according to claim 1, wherein step (a) is conducted in the presence of an organic solvent selected from the group consisting of methylene chloride, pentane, hexane, cyclohexane, toluene, ethyl acetate and tetrahydrofuran.

4. The method according to claim 1, wherein said lithium salt is selected from the group consisting of lithium bromide, lithium chloride, lithium iodide, lithium perchlorate, and lithium fluoroborate.

5. The method according to claim 4, wherein said lithium salt is lithium bromide.

6. The method according to claim 1, wherein step (a) is conducted at a temperature ranging between about 0° and about 60° C. for a period ranging between about 1 hour and about 14 days.

7. The method according to claim 6, wherein step (a) is conducted at a temperature of about 25° C. for about 7 days.

8. The method according to claim 1, wherein said acylating reagent is selected from the group consisting of vinyl acetate, vinyl butyrate, and vinyl valerate.

9. A method for resolving a first optically active isomer and a second optically active isomer from a racemic mixture, without employing chromatography, wherein said first optically active isomer and said second optically active isomer is selected from the group consisting of:

wherein X is selected from the group consisting of alkyl, alkenyl and alkynyl groups having 2 to 10 carbon atoms; and R is selected from the group consisting of —$CH_2OR_1$ and —$CO_2R_2$ wherein $R_1$ is selected from the group consisting of hydrogen, alkyl of 1 to 6 carbon atoms, ethoxyethyl, adamantyl, aryl, heteroaryl, and heterocyclic, and $R_2$ is alkyl of 1 to 6 carbon atoms; said method comprising the steps of:
(a) contacting said racemic mixture with an effective amount of a lipase capable of esterifying an alcohol and an effective amount of a vinyl ester acylating reagent so as to form a resolved mixture containing said first optically active isomer and an acetate derivative of said second optically active isomer;
(b) treating said resolved mixture with a lithium salt in an anhydrous solvent so as to form a lithium salt complex with said first optically active isomer; and
(c) recovering said lithium salt complex.

10. The method according to claim 9, wherein said lipase is porcine pancreatic lipase.

11. The method according to claim 9, wherein step (a) is conducted in the presence of an organic solvent selected from the group consisting of methylene chloride, pentane, hexane, cyclohexane, toluene, ethyl acetate and tetrahydrofuran.

12. The method according to claim 9, wherein step (b) is conducted in the presence of an organic solvent selected from the group consisting of methylene chloride, pentane, hexane, cyclohexane, toluene, ethyl acetate and tetrahydrofuran.

13. The method according to claim 9, wherein said lithium salt is selected from the group consisting of lithium bromide, lithium chloride, lithium iodide, lithium perchlorate, and lithium fluoroborate.

14. The method according to claim 13, wherein said lithium salt is lithium bromide.

15. The method according to claim 14, wherein step (a) is conducted at a temperature of about 25° C. for about 7 hours.

16. The method according to claim 9, wherein step (a) is conducted at a temperature ranging between about 0° and about 60° C. for a period ranging between about 1 hour and about 14 days.

17. The method according to claim 9, wherein said acylating reagent is selected from the group consisting of vinyl acetate, vinyl butyrate, and vinyl valerate.

* * * * *